United States Patent [19]

Saulnier et al.

[11] Patent Number: 5,544,662
[45] Date of Patent: Aug. 13, 1996

[54] HIGH-SPEED ELECTRIC TOMOGRAPHY

[75] Inventors: Gary J. Saulnier, Rexford; David G. Gisser, Albany; Jonathan C. Newell, Glenmont, all of N.Y.; Raymond D. Cook, Reston; John C. Goble, Charlottesville, both of Va.; David Isaacson, Latham, N.Y.

[73] Assignee: Rensselaer Polytechnic Institute, Troy, N.Y.

[21] Appl. No.: 132,457

[22] Filed: Oct. 6, 1993

Related U.S. Application Data

[63] Continuation-in-part of Ser. No. 727,075, Jul. 9, 1991, Pat. No. 5,390,110, Ser. No. 734,591, Jul. 23, 1991, Pat. No. 5,381,333, and Ser. No. 808,795, Dec. 16, 1991, Pat. No. 5,284,142.

[51] Int. Cl.$^6$ .................................................. A61B 5/05
[52] U.S. Cl. ..................................................... 128/734
[58] Field of Search ..................... 128/734; 364/413.13

[56] References Cited

U.S. PATENT DOCUMENTS

| 4,291,708 | 9/1981 | Frei et al. | 128/734 |
| 4,486,835 | 12/1984 | Bai et al. | 128/734 |
| 4,920,490 | 4/1990 | Isaacson | 364/413.13 |
| 5,272,624 | 12/1993 | Gisser et al. | 128/734 |

Primary Examiner—Ruth S. Smith
Attorney, Agent, or Firm—Notaro & Michalos

[57] ABSTRACT

An apparatus for electrical impedance imaging of a body includes an array of multiple electrodes. Each is connected to an adjustable amplitude precision current source of fixed frequency and an oversampling type digital voltmeter. The current amplitudes are set to produce a series of spatial current patterns, all orthogonal to each other, and each applied for only a short time interval while voltages are measured. The voltage and current values are used to create real and reactive impedance images of the interior of the body.

14 Claims, 10 Drawing Sheets

HIGH-SPEED ELECTRIC TOMOGRAPHY

STATEMENT OF GOVERNMENT INTEREST

This invention was made in part with Government support under NIH - National Institute of General Medical Sciences Grant Nos. R01 GM42935 and R01 GM39388.

CROSS REFERENCE TO RELATED APPLICATIONS

The present application is a continuation-in-part application of Ser. No. 07/727,075 filed Jul. 9, 1991 now U.S. Pat. No. 5,390,110; Ser. No. 07/734,591 filed Jul. 23, 1991 now U.S. Pat. No. 5,381,333; and Ser. No. 07/808,795 filed Dec. 16, 1991 now U.S. Pat. No. 5,284,142.

FIELD AND BACKGROUND OF THE INVENTION

The present invention relates in general to electrical impedance tomography, and in particular to a new and useful apparatus for non-invasive clinical diagnosis.

The present invention represents the culmination of a development which can be traced back to the disclosure of U.S. Pat. No. 4,920,490 entitled PROCESS AND APPARATUS FOR DISTINGUISHING CONDUCTIVITIES BY ELECTRIC CURRENT COMPUTED TOMOGRAPHY. One conductivity in a body can be distinguished from another using the teaching of this patent which is incorporated here by reference.

The following co-pending applications which are also incorporated here by reference, track the further development of the invention. Ser. No. 07/591,615 filed Oct. 2, 1990 and entitled CURRENT PATTERNS FOR IMPEDANCE TOMOGRAPHY, discloses now U.S. Pat. No. 5,272,624 a method for creating simplified current patterns for use in impedance imaging.

Ser. No. 07/727,075 filed Jul. 9, 1991 now U.S. Pat. No. 5,390,110 and entitled A LAYER STRIPPING PROCESS FOR IMPEDANCE IMAGING, discloses a method of creating an impedance image, layer by layer into the thickness of a body.

Ser. No. 07/734,591 filed Jul. 23, 1991 now U.S. Pat. No. 5,381,333 and entitled CURRENT PATTERNS FOR ELECTRICAL IMPEDANCE TOMOGRAPHY, discloses an adaptive process for calculating the best current patterns to be applied to the electrodes of a device for creating an impedance image.

Ser. No. 07/808,795 filed Dec. 16, 1991 now U.S. Pat. No. 5,284,142 and entitled THREE-DIMENSIONAL IMPEDANCE IMAGING PROCESSES, discloses a method for mathematically manipulating the voltages or currents measured from an array of electrodes around the body, to form an impedance image of the three dimensional space within the body.

The foregoing patent and pending applications are all incorporated by reference in that they may help better explain the present invention and its usefulness in electrical impedance tomography (EIT) and electric current computed tomography (ECCT).

Although the above-identified patent applications do not represent prior art to the present application, the prior art does contain alternate examples of apparatus and equipment that is useful in the field of tomography.

U.S. Pat. No. , 4,539,640 to Fry, et al. discloses an apparatus and method for impedance imaging of a patient's body utilizing an array of electrodes in electrical contact with the outer surface of the patient's torso. Circuitry disclosed in this patent is capable of multiplexed application of current patterns.

U.S. Pat. No. 4,263,920 to Tasto, et al. also discloses an imaging apparatus which utilizes an array of multiple electrodes for use in measuring resistant paths through a body.

It is also known to use electrical bridges to measure impedance between two distinct points on a body. U.S. Pat. No. 4,911,175 to Shizgal is one example.

U.S. Pat. No. 4, 947,862 to Kelly also discloses an apparatus utilizing electrical contacts on the body for measuring a composition of the body.

SUMMARY OF THE INVENTION

There are a number of methods for producing images of internal structures of a body. Each of the different methods in use is sensitive to some particular aspect of the structures to be imaged. X-rays, for instance, are absorbed to differing degrees by different internal organs, and to the greatest degree by bones. Impedance imaging depends on the fact that various structures or tissues inside a body, e.g. a human body, have differing values of specific electrical resistance and of charge storage capability. The term impedance involves both of these aspects of the electrical properties of matter.

In the present invention, the method by which an impedance image of a body, or section thereof, is produced requires that conducting electrodes be applied to the surface of the body. If a single pair of electrodes are used, and current is made to flow between them, appropriate measurements of the voltage and current can be used to calculate average resistance and reactance values of the region between the electrodes. In order to obtain enough information to produce a resistive or reactive image, many electrodes must be used, and many currents and voltages measured. The essence of tomography is to pass a number of currents through the same small region of the body but in differing directions, so that the impedance of that small region can be calculated. Since the actual current flow in the body does not, in general, travel in straight lines, as x-rays do, the problem of producing an image from the electrical data is more complex than that for x-ray tomography data, for instance. Also, because the impedances of internal structures may vary from an average by a relatively small amount, it is essential that voltage and current values be measured very precisely for the system to be of value.

This invention comprises an improved apparatus for generating a predetermined number of sets of precisely set alternating current values to be applied to a body via external electrodes, and a system for precisely measuring both real and reactive components of voltages, along with other features so that data needed to produce images can be conveniently, safely and quickly obtained. One advantage of this system over conventional imaging methods is its small size and portability. Heavy permanent installations are not needed.

Other advantages of the present invention are in the areas of safety to the patient and high speed operation combined with high precision measurements made in such a way as to maximize the signal-to-noise ratio. Many of these features depend on the presence of a system for generating a separate individually adjusted current value and an apparatus for phase-sensitive voltage measurement for each electrode. The current generators differ in phase from each other only trivially as their amplitude is adjusted. Digital rather than analog circuitry is used whenever possible. An additional advantage is that data for calibratable direct images of real and reactive impedance may be obtained. Many other systems designed for high speed operation are only capable of producing images of the difference in impedances between adjacent "snapshots". Such "difference images" are also available in the present invention, from the data for several images.

The present invention also utilizes synchronized waveform switching as described in a previous disclosure (i.e. Ser. No. 07/591,615 now U.S. Pat. No. 5,272,624), and a compensated voltage-to-current converter in each channel to maintain high internal impedance. The compensation can be trimmed under automatic computer control. Included is an automatic calibration system, also under computer control, which can be used as often as needed to compensate for drifts in component values.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

An embodiment of the invention to be described requires reference to the accompanying drawings in which.

DESCRIPTION OF THE PREFERRED EMBODIMENT

Although there are many applications of impedance imaging in industrial and geologic areas, such as the inspection of parts, detection of cracks, discovery of the presence and position of inhomogeneities in liquids and solids, and location of underground strata, the preferred embodiment of this invention is intended to be used for medical diagnostic applications. When the subjects are humans, purposeful injections of electric current must be done with appropriate safeguards. It is well known that safety is enhanced by the use of low currents, short time periods, and alternating currents with high frequencies of oscillation.

In addition, the time required to obtain the data for a single image must be short compared with the time period of one respiration or one heartbeat if smearing of the image is to be avoided when respiratory or cardiac information is desired. The instrument thus, must introduce a set of relatively small but precisely known currents to the electrodes and measure voltages with great precision at each of the electrodes. A different set of currents is then introduced, and voltages measured. This process is repeated many times in order to obtain data for one image, so the entire process must take only a small fraction of a second.

In the preferred embodiment to be described, the system uses 32 electrodes, the maximum current used in any electrode is a fraction of a milliampere, the frequency of the current is 30 kHz, the voltages to be measured at the electrodes are normally fractions of a volt. The time for one image is 133 ms. During this time, 31 different sets of currents are applied, each for 4.3 ms. During most of the time that a current set is applied, about 4 ms, all 32 voltages are simultaneously measured, both the in-phase and quadrature components, and converted to digital form.

Although the numerical values just mentioned are the approximate values in use in this embodiment, it is to be understood that the instrument design is flexible, and most of the values may be changed without altering the nature of the invention.

Figure 1:
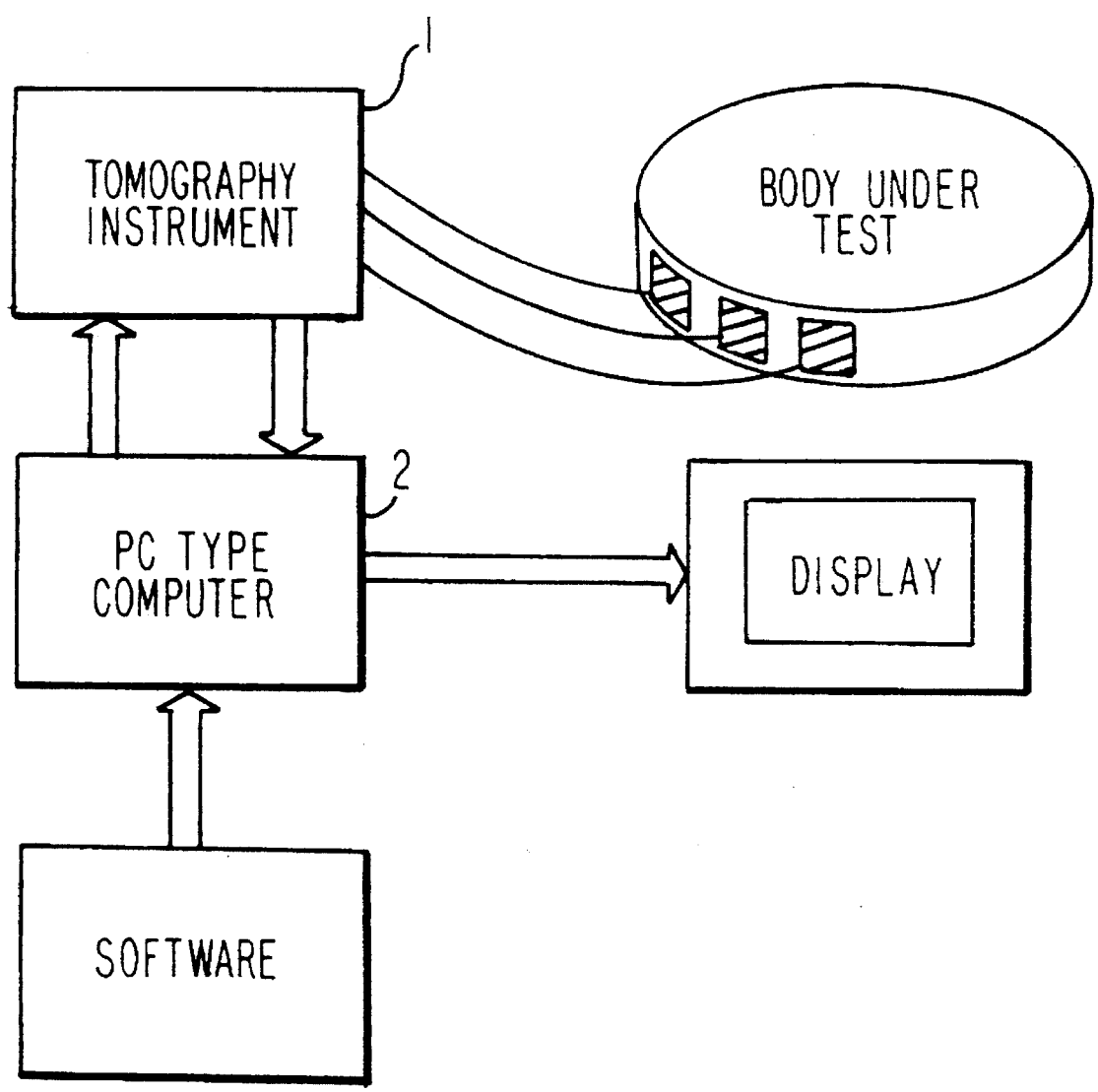
FIG. 1 is a schematic block diagram of the general arrangement of equipment required for producing impedance images of the interior of a body.

FIG. 1 shows the major components of a system for producing impedance images of the interior body. Only three of the many electrodes which normally encircle the body are explicitly shown. The tomography instrument 1 is the main subject of this invention. It is controlled by software stored in the memory of the computer 2 and the tomography instrument contains the components required to produce the needed currents to the electrodes, measure the voltages on the electrodes, and return the digital voltage values that were measured to the memory of the computer, which are in turn used to form an image on a display connected to the computer.

Instrument 1 also contains circuitry for other useful functions as will be described.

Figure 2:
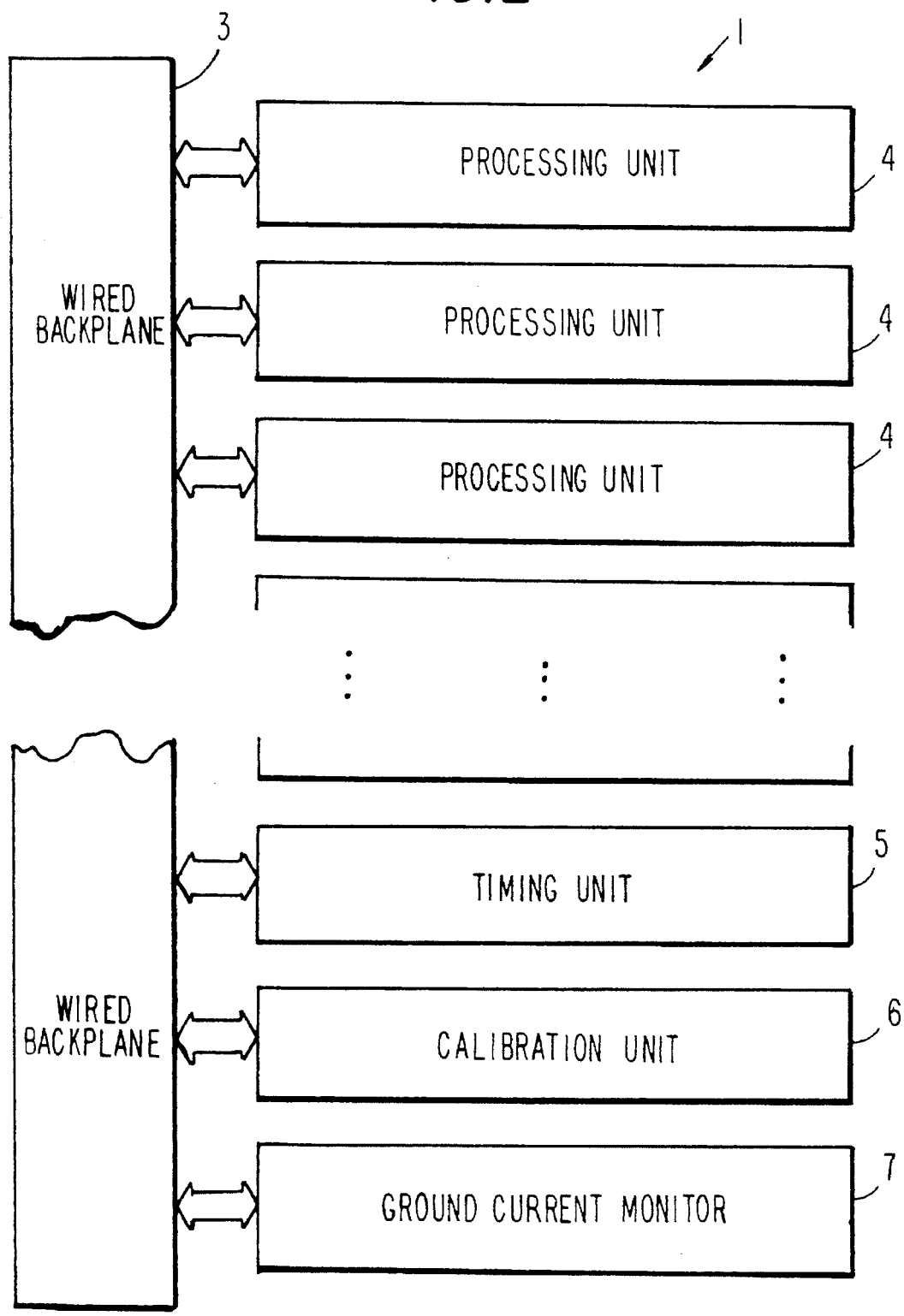
FIG. 2 is a block diagram of the major components of the novel instrument for impedance imaging to be described.

FIG. 2 is a block diagram of the major components of the tomography instrument 1. The components include a wired backplane 3 to which there are connected thirty two identical processing units, 4, one for each electrode. Note that only three of the thirty two are explicitly shown. There is also a timing unit 5, a calibration unit 6, and a ground current monitor unit 7.

The timing unit 5 contains the master clock. The timing unit will be described in greater detail later, with reference to FIG. 3. A number of signals derived from the clock and synchronized to it are distributed to other units via the backplane. Some of these signals are used to control the precise times at which the voltmeters sample input signals. The timing unit also includes a read-only memory system that is programmed so that its parallel digital output value is the trigonometric cosine of the digital input value expressed as a fraction of a cycle. The output bus from this memory is distributed by the backplane to other units where it is needed to generate sinusoidal waveforms.

The processing units 4 (details in FIGS. 4 and 5) are used to produce the sinusoidal voltage waveforms, to modify their amplitudes as required, to convert these voltages into precise currents which can be conveyed to their respective electrodes without degeneration, and to measure the voltage at the associated electrode with respect to the common reference, or, if desired, the voltage difference between adjacent electrodes.

The calibration unit 6 (details in FIG. 9) contains a sinusoidal voltage generator, current-to-voltage converter and a voltmeter system similar to those in the processing units. The calibration unit permits voltage values and, indirectly, currents to be compared with an external standard. Current from any selected processing unit may be measured in this unit, permitting a trim procedure for the processing units to be easily automated.

The ground current monitor 7 (details in FIG. 10) performs an important safety function and is also useful during diagnostic procedures on the system.

The way in which these functions are performed will now be described.

The data for a single (real part) image is provided by thirty one sets of thirty two voltage readings each. An additional thirty two voltage readings for each set are needed for a quadrature image. Each set consists of a particular arrangement of current magnitudes and polarities at the electrodes, which are different from the arrangement used in all other sets. Each set has the required constraint that the sum of all currents should be zero, thus producing a zero ground current.

For simplicity, the most straightforward arrangement will be considered. Assume the 32 numbered electrodes, numbers 1 to 32, are in roughly a circular shape, with the last one adjacent to the first one. Although not necessarily optimum, apply sinusoidal sets of current patterns. The first set consists of a spatial cosine of current sizes. That means that electrode no. 1 will apply the maximum size current of positive polarity. Electrode no. 2 will have a slightly smaller positive polarity current, electrode no. 3 still smaller and so on until electrode no. 9, has current at zero. Electrode no. 10 will have a small negative-polarity current, no. 11 a somewhat larger one and so on up to electrode no. 16, which has nearly the maximum current but with negative polarity. Electrodes no. 17 through 32 have the same magnitude currents as numbers 1 through 16, but of opposite polarity. If the values of the currents are set correctly, the variation of the currents applied, as one traverses the thirty two electrodes, can be described as a spatial cosine.

Before going on to describing the second set of currents, it is noted that the present invention can also be practiced with non-sinusoidal waveforms, as long as the waveforms are repetitive in time (temporal or repetitive current waveforms). The combination of waveforms assembled into a spatial current pattern, also need not be a sinusoidal current pattern. Therefore, while spatial sine and cosine current patterns are discussed in detail, the present invention extends to other spatial current patterns. One example, the Walsh functions described in at least one of the above-identified co-pending patent applications can be used both as the repetitive current waveforms and as the spatial current patterns.

It is further noted that the array of electrodes need not be in the form of a ring around the body or even be in electrical contact with the outer surface of the body only. For example, the electrodes may be applied in separate groups or patches on the outer surface of the body, or even on inner surfaces of the body, for example, within the mouth cavity, or within the stomach, bladder, etc. Further, where a ring of electrodes is utilized around the body, several rings of electrodes can be used in conjunction with each other to produce a three-dimensional image. Returning now to the disclosed embodiment using sinusoidal temporal waveforms formed into spatial sinusoids, the second set of currents will be described.

The second set of currents is similar, but displaced by eight electrodes. They start with zero current at electrode no. 1, a small current at no. 2, building to near maximum at electrode no. 8. From no. 9 to no. 16 the values drop from maximum to near zero. Electrodes no. 17 through 32 have the same magnitudes but opposite polarity from those applied at electrodes no. 1 through 16. The resulting pattern, that is the second set of currents, for correctly adjusted values, can therefore be considered a spatial sine rather than a spatial cosine.

The third set of currents, that is the third current pattern, has a cosine variation, but the polarity of the current changes four times instead of twice when sequencing through all thirty-two electrodes. We refer to it as a spatial cosine of double frequency. The fourth set has currents displaced from the third set by the amount required to produce a spatial sine of double frequency. The remaining patterns of currents consist of approximations to spatial cosines and sines of triple, quadruple, quintuple etc. frequency, until the thirty first set, which has alternating positive and negative maximum size currents on all thirty two electrodes, producing sixteen spatial cycles.

It is necessary, therefore to have means for producing thirty two sinusoidal currents whose amplitudes are quickly, easily and precisely controllable. In addition, the phase angles of all the positive currents should be identical as should be those of the negative currents, and the phase angle of the negative and positive currents should be exactly 180° degrees apart.

These stringent requirements are accomplished in this invention by a number of innovations that will now be described.

Previously disclosed systems of this kind have used a single source, or oscillator, for the relatively high frequency sinusoid needed. Its output was distributed to each of the devices required to provide adjustable value signals to the voltage-to-current converters and hence to the electrodes. These devices were usually multiplying digital-to-analog converters, in order to have easy computer control over the size of each current. Such a system suffers from several difficulties, the most serious of which is that the digital-to-analog converters must operate at relatively high frequencies at which they are inherently unable to maintain the same phase angle for digital inputs of various sizes.

Figure 3:
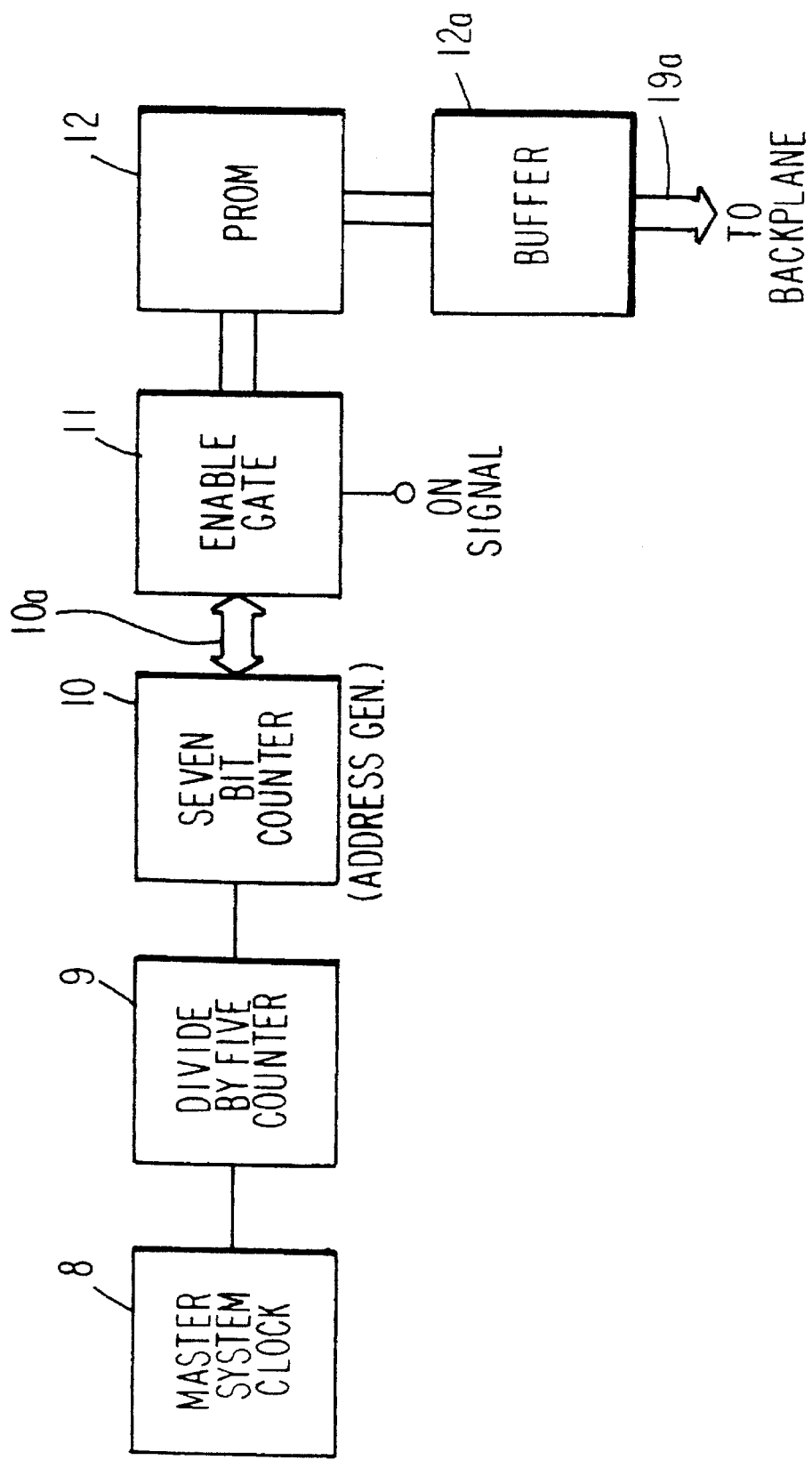
FIG. 3 is a block diagram of the part of the timing unit of the instrument that generates digital codes for synthesizing an analog sinusoid.

The sinusoidal signals in the present invention are digitally generated, separately for each electrode, but all based on the same high frequency timing clock, assuring phase coherence. A portion of this system is common to all the electrodes. It is part of the timing unit 5, and its block diagram is shown in FIG. 3. It consists of a master system clock 8 operating at 18.432 MHz. This frequency is next divided by five in the counter circuit 9 in order to produce 3.686 MHz, which is then used to drive a 7-bit counter 10 used as an address generator that recycles at a 28.8 kHz rate. Of course, by setting the frequency divider to values other than five, other frequencies may be generated.

The seven output lines 10a from the address generator 10 are connected to an enable gate 11 that holds the input address of a digital sinusoid PROM (programmable read only memory) 12 at zero, at all times except intervals when an address enable signal is applied. The PROM is programmed to produce a 10-bit output code for each of its 128 input steps. The output codes are the digital values of the cosine of the input step number as a fraction of a full cycle of 128 steps. In this manner, whenever the address generator 10 is enabled, digital codes whose values represent a sinusoidal variation are available at the PROM output, cycling at the same frequency as the address generator. The digital output is buffered at 12a and becomes digital input signal 19a which is distributed to all the actual analog sine generators via a waveform bus on at the backplane 3. Notice that the time of the cycle at which the PROM begins or ends its output variations may be set to any of 128 values and is synchronized with the system clock 8. Thus, currents at a positive or negative peak can easily and accurately be applied to all electrodes simultaneously.

Figure 4:
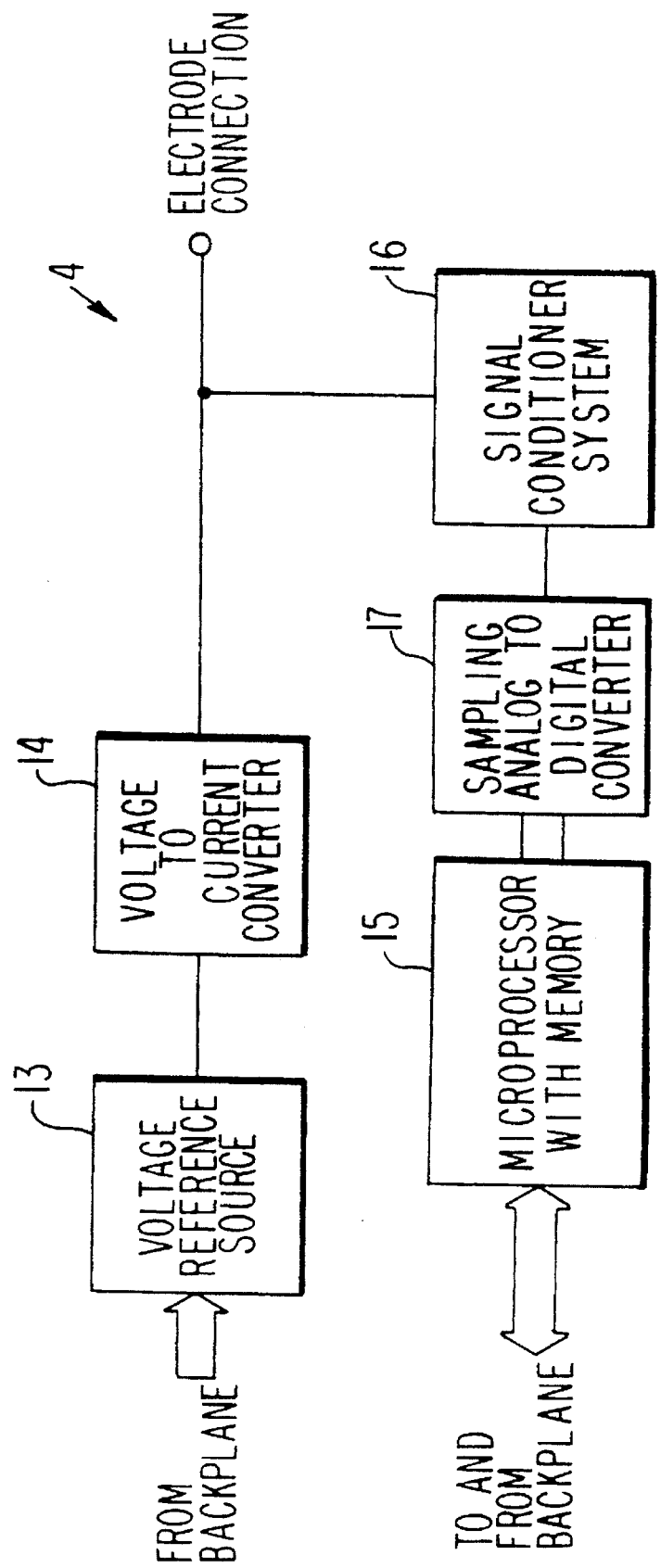
FIG. 4 is a block diagram of one of the 32 processing units used in the instrument, one for each electrode.
Figure 5:
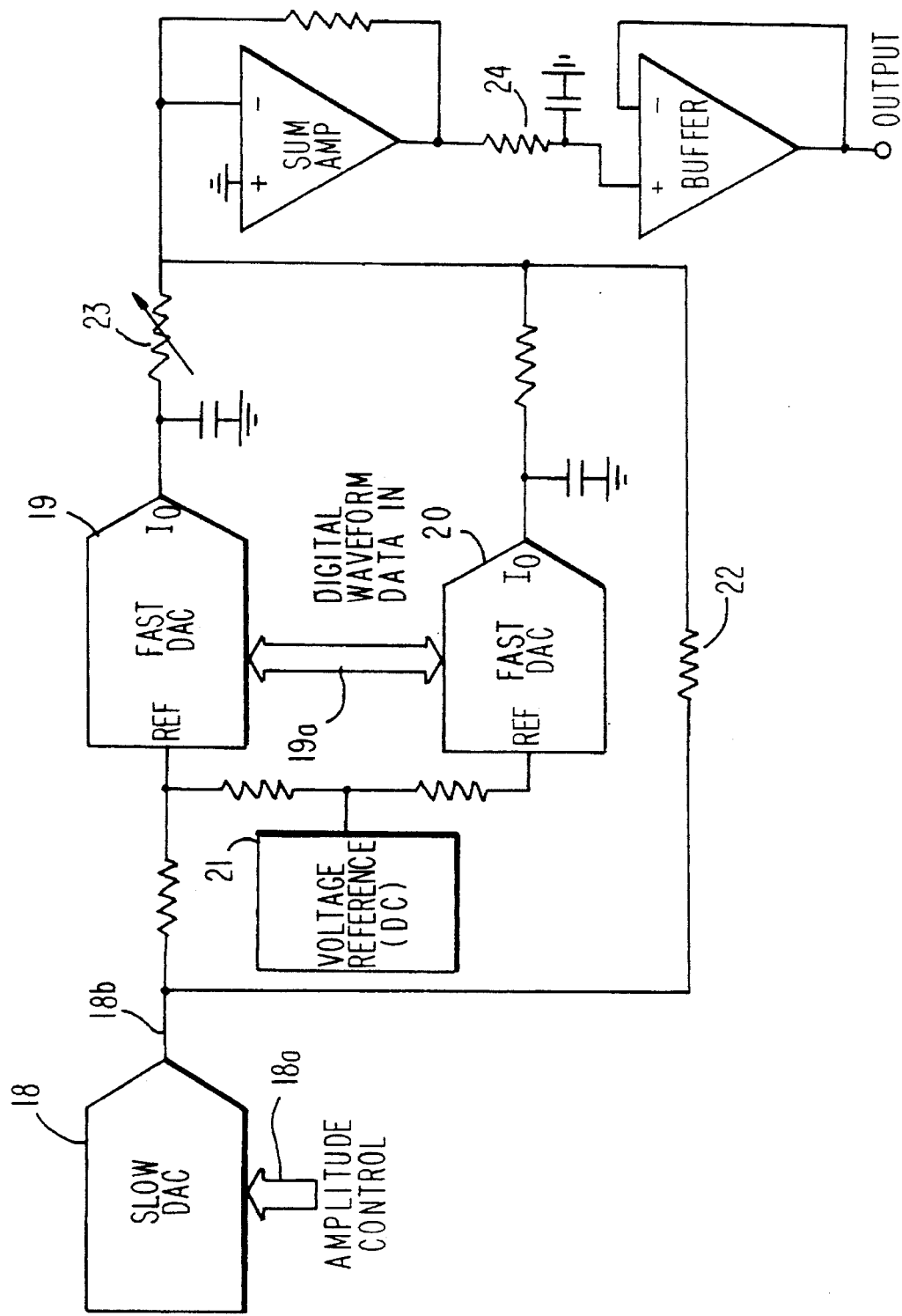
FIG. 5 is a block diagram of the effective four quadrant multiplying digital-to-analog converter used in each of the processing units to produce adjustable magnitude and polarity sinusoids.

A block diagram for one of the thirty two identical processing units 4, is shown in FIG. 4. Each contains a voltage reference source 13, a compensated voltage-to-current converter 14, a controlling microprocessor with memory 15, a signal conditioner system 16 and a high-speed sampling analog-to-digital converter 17.

Each voltage reference source (see FIG. 5), changes the stream of digital codes from the waveform bus into an analog voltage signal whose amplitude may be set as desired. This is accomplished in the present invention by the use of three digital-to-analog converters. The first is a low-speed but linear and stable two-quadrant device 18. Its digital input 18a determines the current amplitude and polarity. The input is a 16-bit word for each of the current patterns to be used, all stored in the memory of the local microprocessor 15. The converter output 18b is a positive or negative DC voltage which is maintained for the time a particular current pattern is in use, about 4.3 ms. Note that this converter is not required to operate at the 30 kHz frequency of the voltage reference source.

The other two digital-to-analog converters 19 and 20 are multiplying 10-bit devices designed for high speed operation. The digital input signal 19a is the buffered output of the PROM 12 (FIG. 3). The DAC 19 is basically biased by the voltage reference 21, but the bias is modulated by the output of the low-speed DAC 18. The DAC 20 has a fixed bias from the voltage reference. When the output current of the one of the these DACs is added to the complementary output current of the other, the output current sum varies from a maximum positive value when DAC 18 output is at a maximum to a maximum negative value when DAC 18 output is at a minimum value, as the digital values on the waveform bus progress. While the circuit inherently rejects offsets, the addition of feedforward resistor 22 reduces them further, and the trimming resistor 23 permits adjusting for essentially zero phase variation with digital code by balancing the circuit at high frequencies. An additional low-pass filter circuit 24 reduces quantization noise and makes the output waveform closely match the analog sinusoid it is designed to emulate.

Figure 6B:
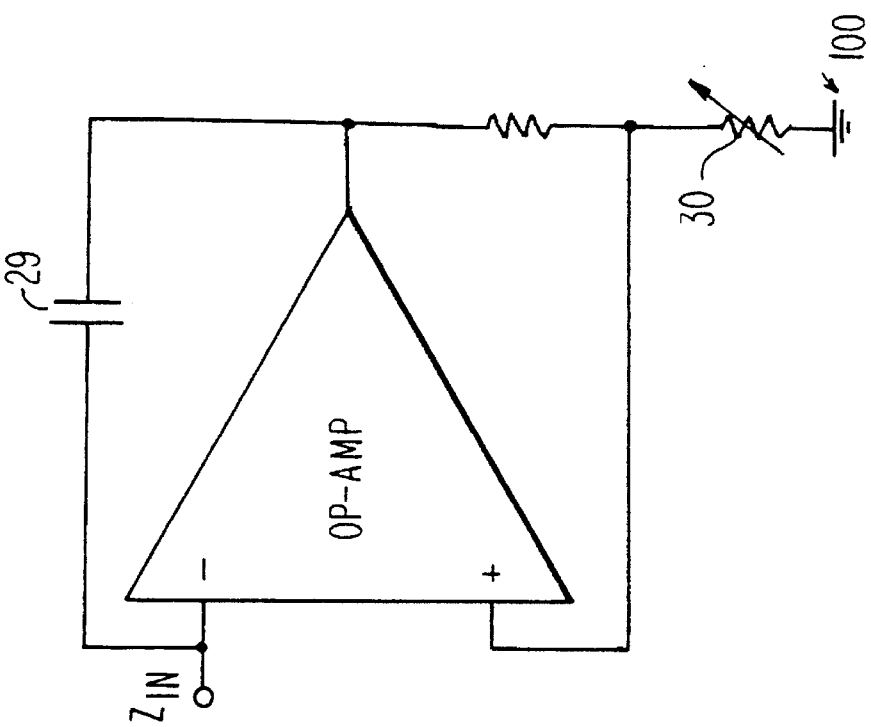
FIG. 6b is a simplified circuit diagram of the adjustable negative capacitance circuit used in each processing unit to compensate unavoidable positive capacitance.
Figure 6A:
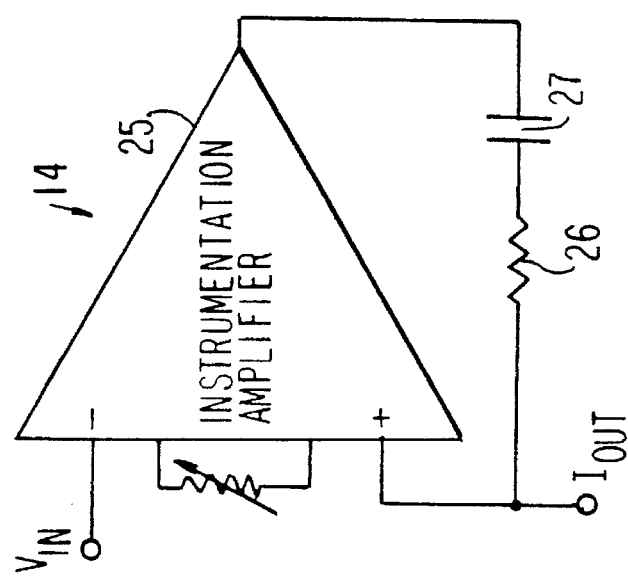
FIG. 6a is a simplified circuit diagram of the voltage-to-current converter used in each processing unit.

The simplified circuit diagram for the compensated voltage-to-current converter system 14 is shown in FIG. 6a. It consists basically of a unity gain instrumentation amplifier 25. The output current is ideally constant with changing loads at a value given by the input voltage divided by the resistance 26 at frequencies where the DC blocking capacity 27 acts as nearly a short circuit. Unfortunately, instrumentation amplifiers are far from ideal, and exhibit considerable internal phase shift at frequencies as high as 30 kHz. As a result, the basic voltage-to-current converter circuit exhibits variation of its output current with changing load. This effect is usually expressed as an internal impedance. The internal impedance at the frequency of operation can be represented as a parallel combination of a resistance and a negative capacitance. By varying the gain of the instrumentation amplifier from its nominal value of one, the internal resistance at any frequency can be adjusted to values that are positive, negative, or infinite.

One of the requirements for the system is that electrode currents must not depend upon electrode voltages to more than a very minor extent. In terms of the impedance that an electrode disconnected from its load sees, the resistance value should be greater than thirty megohms and the equivalent shunt capacitance should be less than 0.5 pf. Because there are several large but finite shunt resistors needed at each electrode to practically implement the voltmeter circuit, and there is considerable accidental capacitance, compensating the voltage-to-current converter circuit to make its internal impedance infinite would not be satisfactory. Instead, the compensation should be for all shunt elements, so that the electrode itself is driven from an equivalent current source that is nearly ideal, that is, of near infinite internal impedance.

This is accomplished in the present invention by adjusting the equivalent shunt internal resistance of the voltage-to-current converter to be equal in value and opposite in sign to the total shunt resistance effectively connected to the electrode when the electrode is not connected to a body to be imaged. The internal resistance adjustment is made by altering the gain of the instrumentation amplifier slightly around its normal value of unity. This gain adjustment is made by a digitally adjustable resistor 28, using a system to be described.

The unavoidable capacitances at each electrode are compensated partly by the previously mentioned negative internal capacitance of the voltage-to-current converter and partly by adding the adjustable negative capacitance circuit using an op-amp, FIG. 6b, in parallel with each electrode. The input impedance of this circuit, assuming ideal components, is the value of the feedback capacitor 29 divided by one minus the op-amp circuit gain. The adjustable resistor 30 controls the op-amp circuit gain and has one thermal connected to common ground 100. This gain is normally set at about two, so that the input impedance appears as a negative capacitance about equal in value to the capacitance of the capacitor 29. The resistance 30, is, like 28, digitally adjustable. By proper selection of component values, adjustments of the resistors 28 and 30 can raise the apparent internal impedance of the effective current source at the electrode to extremely high values.

Figure 7:
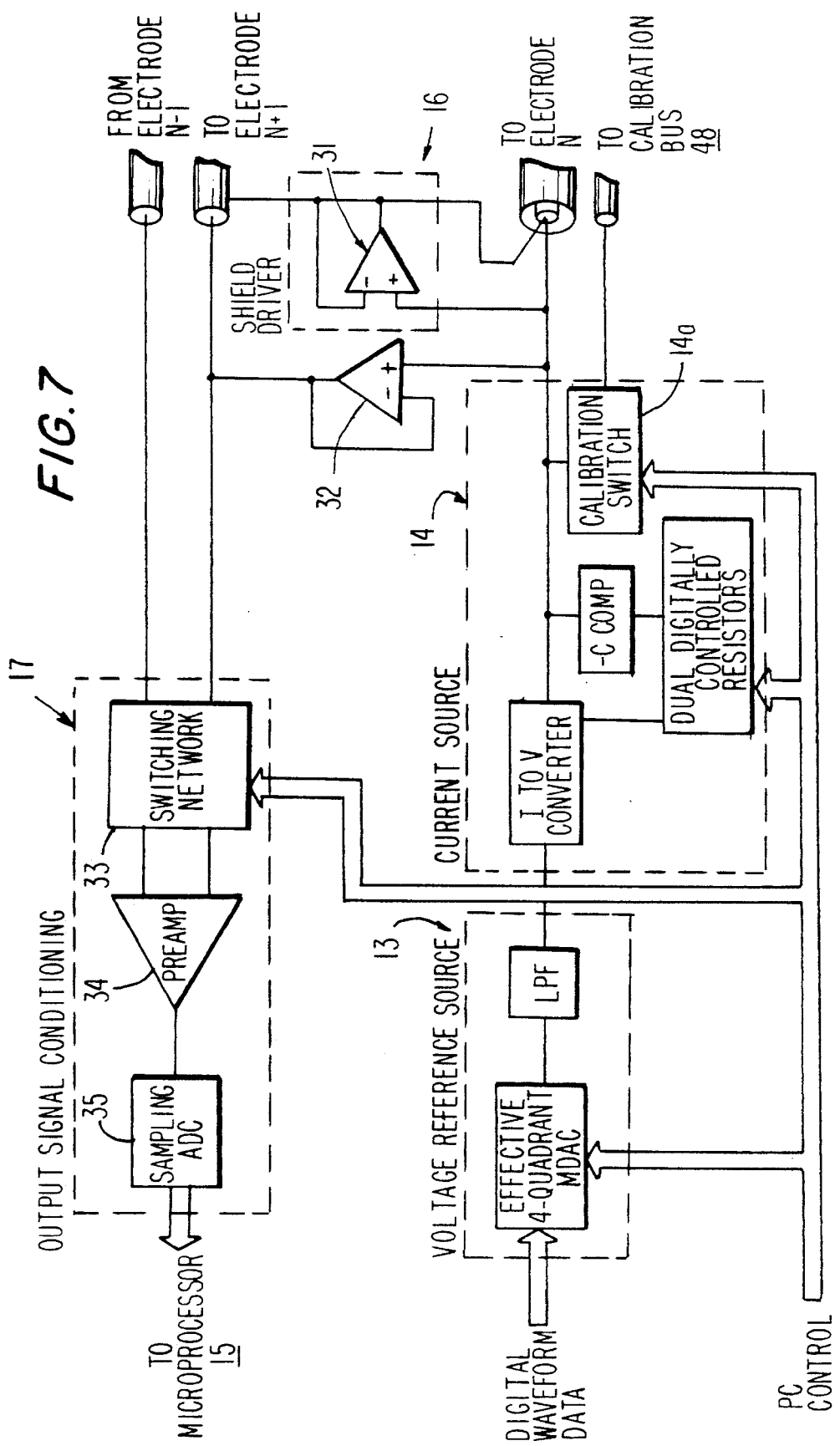
FIG. 7 is a partial block diagram showing more details of the portion of FIG. 4 adjacent to the electrode cable.

The relationship between the components in the block diagram of FIG. 4 is more clearly illustrated in FIG. 7, in which unity gain connected op-amps 31 and 32 are shown. Op-amp 31 is used to drive the cable shields of both the electrode n, connected to the processing unit n as well as the shield of the cable that goes to the next numbered electrode, n+1. (It is to be understood that when n is the last numbered electrode, n+1 is the first electrode.) Op-amp 32 is used as a unity gain buffer to provide a voltage signal to the switching network 33 without loading down the effective electrode current source. Note that the current source 14 may be connected to the calibration bus 48, and thence to the calibration unit 6 whenever desired without disconnecting the electrode cable, by a calibration switch 14a.

The purpose of the switching network 33 is to permit the preamplifier 34 to measure either the voltage at the electrode n with respect to the common ground or to measure the voltage difference between the electrode n and electrode n+1. The switching network 33 and the calibration switch 14a all consist of reed relay contacts. The reed relay coils are driven by signals from the computer 2, amplified by solid-state devices.

The function of the preamplifier 34 is to increase the voltage signals available to levels appropriate for the sampling analog-to-digital converter 35. The purpose of the converter is to change the magnitude of the alternating voltage from the preamplifier into a commensurate digital value in the very short time allowed with as high a ratio of signal-to-noise as possible.

The traditional method for measuring an AC voltage is to first change it into a DC form, and then measure the DC value. If the conversion is performed by simple rectification, any phase information is lost. If a phase reference signal is available of exactly the same frequency as the signal to be measured, the expedient of multiplying the signal to be measured by the reference sinusoid produces a signal whose average or DC value is proportional to the component of the signal to be measured that is in phase with the reference, and which has very little sensitivity to signal or noise components at other frequencies. If the multiplying signal is phase-shifted by ninety degrees, the average value is proportional to the quadrature (with respect to the reference) component of the signal to be measured. This method unfortunately requires considerable low-pass filtering, which takes time, in order to measure the average values. In addition, there is the disadvantage that the needed filters normally produce a time average that is most heavily weighted by the most recent events.

In the present invention, the signal to be measured is not first converted to DC. Instead, the AC signal is effectively sampled and converted to digital form at a multitude of points in a cycle, say 360 points, one degree apart. The digital value of the sine of 1° is then multitude by the first sample, the sine of 2° by the second, etc. An averaging operation may now be accomplished by merely adding up all the multiplication products, resulting in a digital number proportional to the in-phase component of the sampled signal. By using digital values of the cosine instead of the sine for multiplication, the quadrature component would be obtained. These multiplication and summation operations are very easy to implement precisely and quickly in digital form using a simple microprocessor, whereas analog multipliers are notoriously non-linear and unstable.

Although the basic idea has just been described, it is not reasonable to sample and digitize to 12 bits a 30 kHz signal at several hundred consecutive points within one of its cycles with devices available at present. Consequently there are actually only five samples taken for each of 128 consecutive cycles, resulting in a total of six hundred forty samples. Furthermore, the time positions of the five samples are not the same in each cycle, but are gradually delayed in time at a rate such that at the end of the last cycle, the 640 samples that have been taken and digitized at 12 bits each are the equivalent of 640 samples of a single cycle. Under these conditions the overall system then produces a theoretically optimum ratio of signal to noise for the number of samples being used, an arrangement sometimes called a "matched filter", in which the ratio of peak signal power to mean noise power is greatest.

Figure 8:
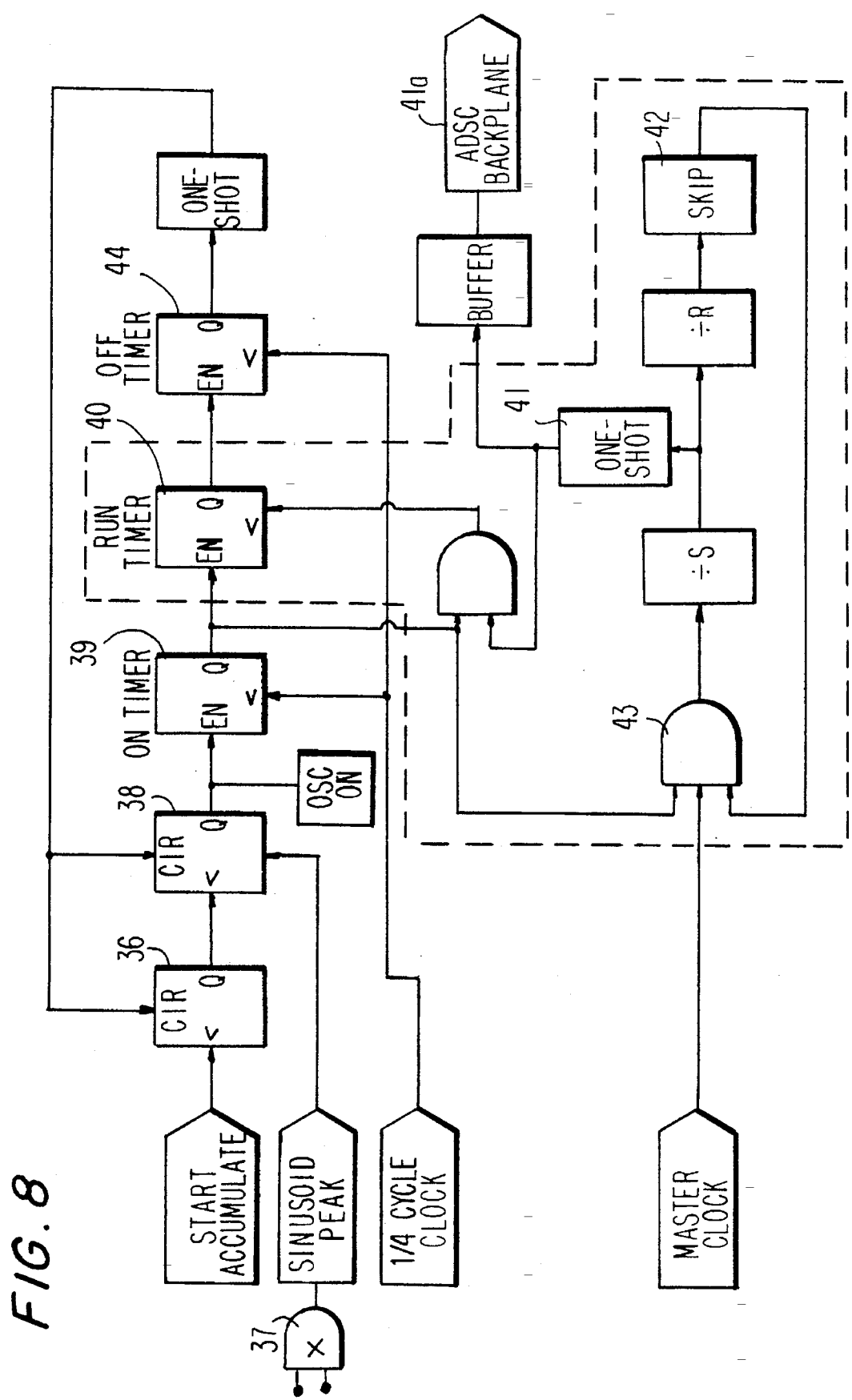
FIG. 8 is a block diagram which shows how the variably spaced timing signals for all the high speed sampling analog-to-digital converters are produced.

A separate preamplifier 34, sampling analog-to-digital converter 35, and microprocessor 15 are employed for each of the processing units. However, the sampling time signals required by each of the sampling analog-to-digital converters are all identical. They originate in the timing unit 5 and are distributed to the processing units via the backplane wiring. A simplified block diagram of the portion of the timing unit dedicated to this purpose is shown in FIG. 8. The sequence of events is as follows. First a signal from the controlling computer sets a flip-flop 36 thereby placing the timing generation subsystem in standby mode. The actual signal to start is derived from the output of the exclusive OR circuit 37 which is driven from the two most significant bits of the digital sinusoid PROM address from the timing unit 5. The peak point of the digital sinusoid, marked by the rising edge of the exclusive OR output, then triggers the flipflop 38 which in turn operates the enable gate of circuit 11 (FIG. 3), thus activating the PROM address bus 19a, to initiate the actual flow of current to all the electrodes.

Flipflop 38 also enables the On-delay timer 39, which counts a presettable number of quarter cycles of the sinusoid by using the MSB-2 line from the address generator 10 as its trigger. The purpose of this timer or counter, is to introduce an appropriate delay after the currents are applied to the electrodes before any voltage measurements are made. This insures that any short-time transients that might be induced by the precipitous onset of current flow can decay enough so that measurement results are valid.

After the required number of quarter-cycles, the Run timer 40 is triggered. It will stay on for the voltage sampling time duration. Sampler pulses are now generated by the one-shot 41 every 128 master clock pulses. The sampler pulses are buffered and connected to the backplane at 41a for distribution. After every five sampler pulses, a signal to the skip circuit 42 causes the gate 43 to fail to pass on the next master clock signal, so the next five sampler pulses are delayed by one master clock interval compared with the first five. In a similar way, the third set are delayed compared with the second, and so on. In this way, a non-uniform sampling generator is made to produce an apparently uniformly spaced set of points.

The Run timer 40 counts the actual number of sampler pulses generated. After 640 such pulses, its output goes low, the master clock signals are inhibited from producing any more sampler pulses by gate 43, and the Off-delay timer 44 is enabled. The On-delay timer is also presettable. By setting the sum of the delays of the On-delay timer and the Off-delay timer to a multiple of four quarter cycles, the enable circuit 11 can be made to stop electrode currents from flowing as well as start them, at a peak point in their waveform. When the Off-delay timer 44 has finished, it clears flipflops 36 and 38 and the system is ready for the process described, to be repeated.

One full cycle of the waveform is considered to consist of 640 equally spaced time steps resulting in 640 angles. The cosine of each of these in digital form is stored in the microprocessor 15 memory. A pre-loaded program causes the microprocessor 15 to multiply each of the 640 digital numbers as they arrive by the appropriate stored cosine value and to accumulate the sum of the products. Almost simultaneously, each is multiplied by the stored sine value and that sum is also accumulated.

The rounded-off sums from several hundred such sets of measurements are stored in the microprocessor memory, and later sent to the controlling computer 2 for processing into images.

Figure 9:
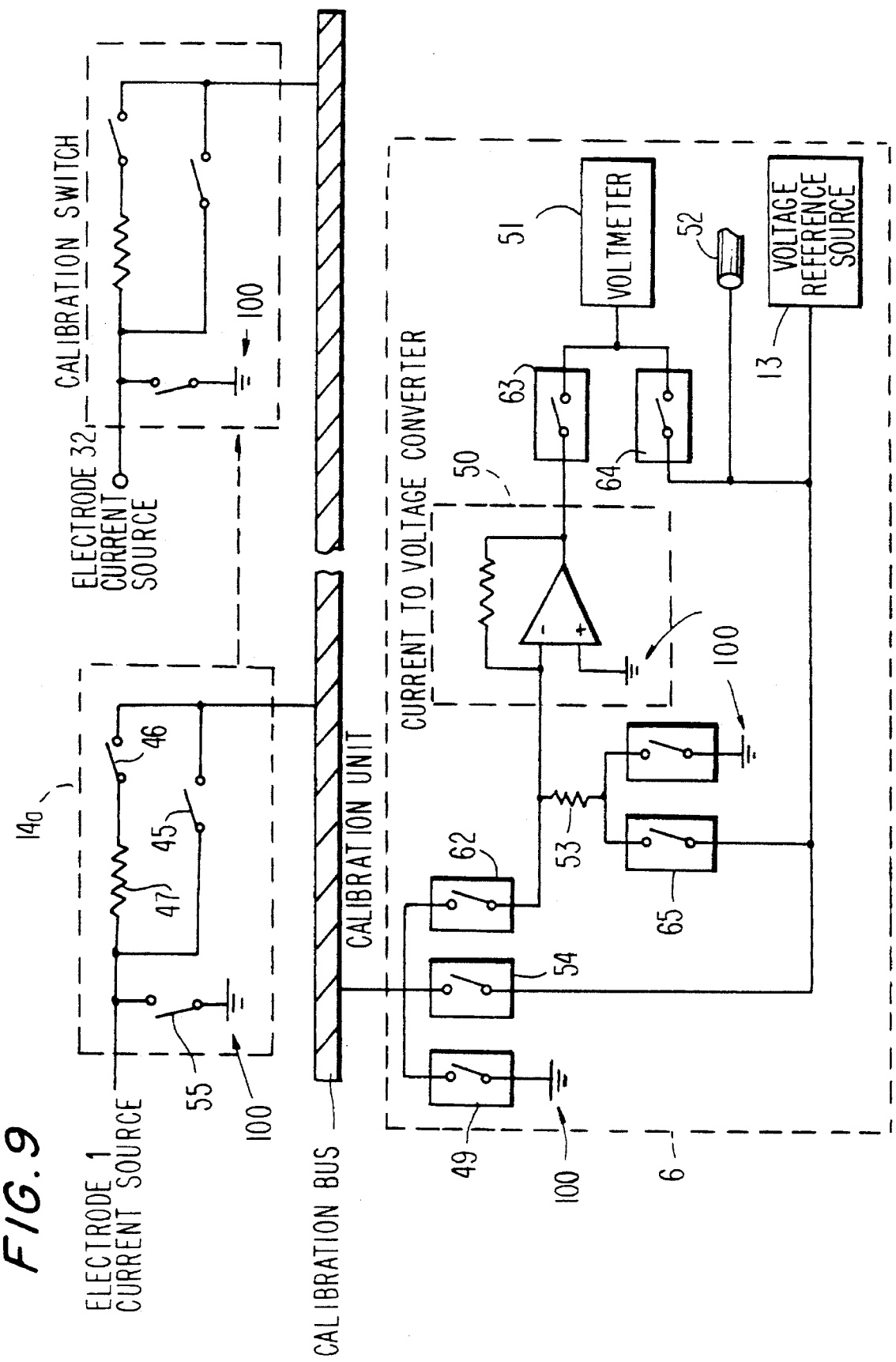
FIG. 9 is a block diagram illustrating the major components of the calibrating system.

An important and useful feature of the present invention is the inclusion of a system that automates and speeds the steps needed to calibrate the overall system and to make any adjustments required. FIG. 9 is a block diagram of the calibration unit 6 and, shows how this is done. Whenever any or all of the electrodes are disconnected from the body under test, as occurs during some of the calibration procedure or while a patient is being connected, the current output of each processing unit 4, if any, is made to pass through a closed reed-relay contact 45. When required, however, contact 45 may be opened, and reed-relay contact 46 closed, which diverts the current flow through a resistor 47 before reaching the calibration bus 48, which is common to all of the processing units. In the calibration unit the reed-relay contact 49 is closed, permitting a path to the common ground 100 for all currents generated. Thus a short-circuit appears from each electrode to ground. The short-circuit is disconnected only when adjustments are made or data is taken. An additional short circuit across the current generator, reed-relay contact 55 is part of a patient protection scheme, to be described shortly.

The remainder of the calibration unit 6 contains a set of reed relay switch contacts, and a current-to-voltage converter 50. There is also a voltage reference source 13 and a sampling voltmeter 51 both identical to those in each of the thirty-two processing units 4.

By appropriate operations of the switches, it is possible to perform the following operations. The output of the voltage reference source 13 may be measured by an external voltmeter connected to the terminal 52 and simultaneously by the voltmeter 51 when contact 64 is closed. This permits a correction curve to be obtained if needed, comparing the internal with the external, or standard voltmeter. When the contacts 54 and 45 are closed the voltage reference source also feeds all the electrodes, and each of their voltmeter readings may then also be compared with the external, or standard.

With contacts 63 and 65 closed, the resistor 53, whose value is carefully determined in advanced, converts the known output of the voltage reference source to a known current, which is then applied to the current-to-voltage converter 50 and measured by the voltmeter 51. With contacts 63 closed, any currents now introduced to the current-to-voltage converter 50 through the switch 62 may now have their values determined from the voltmeter output and the calibration data just collected. Notice that both real and quadrature measurements are made, so any phase shift associated with the current-to-voltage converter of the voltmeter or its preamplifier can be accounted for. Also note that any calibration bus capacitances have essentially no effect since the bus is at the nominally zero voltage of the current-to-voltage converter summing junction.

The procedure for adjusting the negative capacitance and equivalent negative resistance for each electrode will now be described. It is based on the fact that an ideal current generator will produce the same current through a short circuit as through a resistor. A non-ideal current generator will produce a different current through a resistor, when its output voltage is non-zero, than for the shorted, or zero voltage, condition. The procedure is normally carried out by disconnecting all electrodes from any loads but leaving the guarded load cable connected, since it may contribute to the capacitance loading the current source. All electrodes are also disconnected from the calibration bus by opening contacts 45 and 46, and their outputs shorted to a common ground 100 by closing contacts 55 except for the single electrode whose current source is to be trimmed for which both contacts 45 and 46 are closed and contacts 55 are open.

Contacts 45, 46, 52, 54 and 63 are closed. The processing unit to be trimmed is commanded to continuously generate any convenient value of current near the maximum, and the real part of the current, as read by the voltmeter 51 is determined. When contact 45 is opened, the current indicated by the voltmeter 51 drops slightly if there is a real positive internal resistance, or rises slightly if internal resistance is negative. The digitally controlled adjustable resistor 28 is now adjusted to restore the voltmeter indication to a value as close as possible to the preceding one. Next, the quadrature output from voltmeter 51 is monitored while contacts 45 are closed and then opened, and the digitally controlled adjustable resistor to produce the same output voltage for both cases.

These two procedures, for the real and quadrature components, may then be repeated in order to obtain an effective internal impedance that is extremely high. The same procedure is now repeated for another electrode, and then another, until all have been trimmed. Digital signals from the controlling computer 2 operate the digitally controllable adjustable resistors and control the reed relays, so the entire process, while consisting of many steps, is easy to automate with a software program, and can be completed in a very short time.

Figure 10:
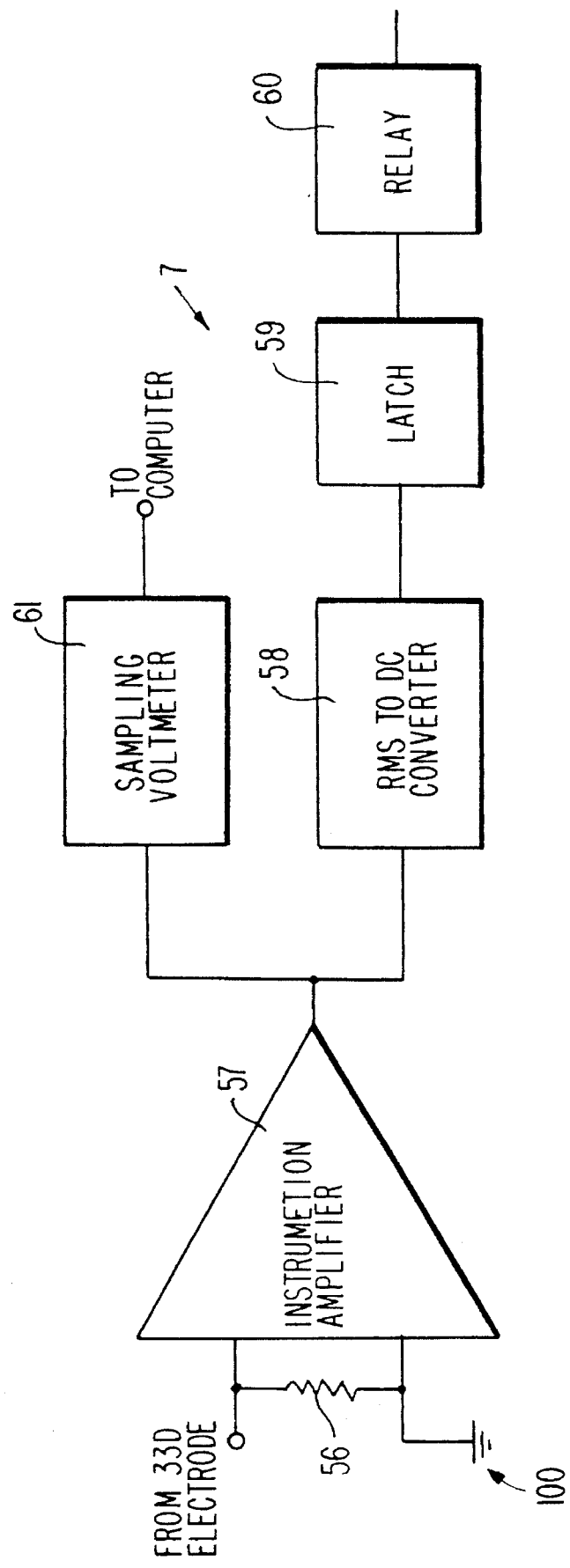
FIG. 10 is a block diagram which shows the major components of the ground current monitoring system.

The present invention also includes a ground current monitoring unit 7. Its block diagram is shown in FIG. 10. It enhances patient safety by diverting the current from the current sources away from the patient if any of several types of fault conditions occur. For example, if an electrode should become detached from a patient, or if a current source fails to operate, or produces a current different from normal, an abnormal value of the ground current will be detected by the ground current monitoring unit.

This is done by providing an extra electrode, (no. 33), to carry any residual current produced by an imbalance of the net positive and net negative currents to the common ground 100. This extra electrode is usually connected to a part of the patient far from the thirty-two active electrodes, such as a leg, when imaging the thorax. There then could be a small but finite current flowing out of the plane of the active electrodes toward the thirty-third electrode. This current may distort the images to be produced, and therefore should be reduced as much as possible.

The current from the extra electrode flows through the current sensing resistor 56 before reaching the common ground, producing a voltage drop. The instrumentation amplifier 57 raises the signal level and the RMS-to-DC converter 58 changes the signal to a DC level that triggers the latch 59 if a presettable threshold is exceeded. The latch drives a relay 60 whose contacts are in series with the power supply for all of the reed relays 55, which short circuits the current sources when de-energized. Notice that this a wideband system, so that currents at any frequency may be detected.

The output of amplifier 57 also drives a sampling voltmeter 61, identical to those in the processing units 4. The voltmeter output is quite insensitive to frequencies other than the one used for the current generator and sampling system.

Although the application described here has been for an instrument with a set of electrodes in a single plane, to be used as an aid in medical diagnosis and treatment, it is clear that the extension to a three-dimensional array of electrodes is straightforward, and applications other than those specifically described may well benefit from this invention.

While a specific embodiment of the invention has been shown and described in detail to illustrate the application of the principles of the invention, it will be understood that the invention may be embodied otherwise without departing from such principles.

What is claimed is:

1. An apparatus for electrical impedance imaging of a body, comprising:

a plurality of electrodes in an array and adapted to be in electrical contact with the body;

waveform means for supplying a plurality of voltage waveforms;

a plurality of voltage-to-current converters connected to the waveform means for receiving the voltage waveforms, each converter being separately connected to each electrode for applying a repetitive current waveform to each respective electrode, all of said repetitive current waveforms together forming a spatial current pattern for application to the array to generate voltage signals at the electrodes with respect to a common ground, for use in forming an electrical impedance image of at least part of a volume in the body;

control means for operating each of said voltage-to-current converters to apply the repetitive current waveforms to the current patterns in synchronism to said electrodes a multiplicity of times, said control means including said waveform means for generating, applying and removing a plurality of repetitive waveforms to and from all of said voltage-to-current converters simultaneously to power said plurality of electrodes simultaneously, said waveform means having a single master clock for use with all of said voltage-to-current converters and a common read-only memory with a digitally stored sinusoid for use in providing the repetitive waveforms;

separate voltmeter means connected to each electrode for measuring individual voltages at each electrode with respect to the common ground due to the multiplicity of concurrent patterns for use in imaging at least part of the volume of the body;

image means for receiving the voltages and forming an impedance image therefrom; and digital-to-analog converter means connected to each voltage-to-current converter and forming part of a voltage reference source for each voltage-to-current converter, each digital-to-analog converter means comprising at least one high-speed digital-to-analog converter for determining a shape of the waveform according to values of a sequence of digital words applied consecutively at a uniform rate to an input of the voltage-to-current converter, and repeated for each cycle of the repetitive waveform, each high-speed digital-to-analog converter connected to an output of a low-speed digital-to-analog converter, the low-speed digital-to-analog converter for determining an amplitude and polarity of the waveform according to values of a separate digital word and forming a reference voltage at the output.

2. An apparatus according to claim 1, including synchronization means for applying and removing the repetitive waveforms to and from the plurality of electrodes at a peak of the repetitive waveform.

3. An apparatus according to claim 1, wherein said voltmeter means comprises a separate digital voltmeter for each electrode, each voltmeter acting as a matched filter for receiving voltage signals from each respective one of said plurality of electrodes.

4. An apparatus according to claim 3, wherein each digital voltmeter includes means for sampling and digitizing the electrode voltage a multiplicity of times during each cycle of a repetitive waveform and for a multiplicity of waveform cycles.

5. An apparatus according to claim 4, wherein the sampling and digitizing means takes samples at sampling points within each waveform cycle which are equally spaced but at different relative locations in successive waveform cycles, so that an aggregate of points sampled effectively constitutes a close and uniformly spaced sampling of a single cycle of the repetitive waveform.

6. An apparatus according to claim 5 including means for producing both real and quadrature voltage data from each aggregate of sampled points, resulting in a pair of images for each set of applied current patterns.

7. An apparatus according to claim 1, including a calibration voltage source connected to said control means, having a constant amplitude and acting as a reference, and switch means connected to the calibration voltage source for applying the reference to each of said electrodes separately for calibrating each separate voltmeter means separately.

8. An apparatus for electrical impedance imaging of a body, comprising:

a plurality of electrodes in an array and adapted to be in electrical contact with the body;

waveform means for supplying a plurality of voltage waveforms;

a plurality of voltage-to-current converters connected to the waveform means for receiving the voltage waveforms, each converter being separately connected to each electrode for applying a repetitive current waveform to each respective electrode, all of said repetitive current waveforms together forming a spatial current pattern for application to the array to generate voltage signals at the electrodes with respect to a common ground, for use in forming an electrical impedance image of at least part of a volume in the body;

control means for operating each of said voltage-to-current converters to apply the repetitive current waveforms to the current patterns in synchronism to said electrodes a multiplicity of times, said control means including said waveform means for generating, applying and removing a plurality of repetitive waveforms to and from all of said voltage-to-current converters simultaneously to power said plurality of electrodes simultaneously, said waveform means having a single master clock for use with all of said voltage-to-current converters and a common read-only memory with a digitally stored sinusoid for use in providing the repetitive waveforms;

separate voltmeter means connected to each electrode for measuring individual voltages at each electrode with respect to the common ground due to the multiplicity of concurrent patterns for use in imaging at least part of the volume of the body; and image means for receiving the voltages and forming an impedance image therefrom;

each voltage-to-current converter including an output terminal, and means for introducing an adjustable negative resistance and an adjustable negative capacitance to the output terminal of each voltage-to-current converter, for establishing an effective high internal impedance for each voltage-to-current converter.

9. An apparatus according to claim 8, wherein each means for introducing adjustable negative resistance and negative capacitance to the output terminal of each voltage-to-current converter is a digitally adjustable and computer-controlled unit.

10. An apparatus according to claim 9, further comprising:

means for sensing a relative size and polarity of a real component and a quadrature component of an internal impedance of each voltage-to-current converter; and means for using the sensed relative size and polarity of the real component and the quadrature component to maximize the internal impedance of each digitally adjustable, computer-controlled voltage-to-current converter.

11. An apparatus for electrical impedance imaging of a body, comprising:

a plurality of electrodes in an array and adapted to be in electrical contact with the body;

waveform means for supplying a plurality of voltage waveforms;

a plurality of voltage-to-current converters connected to the waveform means for receiving the voltage waveforms, each converter being separately connected to each electrode for applying a repetitive current waveform to each respective electrode, all of said repetitive current waveforms together forming a spatial current pattern for application to the array to generate voltage signals at the electrodes with respect to a common ground, for use in forming an electrical impedance image of at least part of a volume in the body;

control means for operating each of said voltage-to-current converters to apply the repetitive current waveforms to the current patterns in synchronism to said electrodes a multiplicity of times, said control means including said waveform means for generating, applying and removing a plurality of repetitive waveforms to and from all of said voltage-to-current converters simultaneously to power said plurality of electrodes simultaneously, said waveform means having a single master clock for use with all of said voltage-to-current converters and a common read-only memory with a digitally stored sinusoid for use in providing the repetitive waveforms;

separate voltmeter means connected to each electrode for measuring individual voltages at each electrode with respect to the common ground due to the multiplicity of concurrent patterns for use in imaging at least part of the volume of the body;

image means for receiving the voltages and forming an impedance image therefrom; and a reference electrode separate from said plurality of electrodes forming said array, current-to-voltage resistor means connected to said reference electrode for measuring voltage at said reference electrode with respect to the common ground, a separate voltmeter connected to said current-to-voltage resistor for measuring a voltage proportional to the current in said reference electrode, and means for interrupting operation of each of the voltage-to-current converters upon detecting a current in the reference electrode exceeding a preset minimum value.

12. An apparatus according to claim 11, wherein said means for interrupting comprises a power supply relay for interrupting power to each of the voltage-to-current converters, a latch connected to said relay for operating the relay, and RMS signal detection means connected to said latch for processing the voltage proportional to the current in said reference electrode.

13. An apparatus for electrical impedance imaging of a body, comprising:

a plurality of electrodes in an array and adapted to be in electrical contact with the body;

waveform means for supplying a plurality of voltage waveforms;

a plurality of voltage-to-current converters connected to the waveform means for receiving the voltage waveforms, each converter being separately connected to each electrode for applying a repetitive current waveform to each respective electrode, all of said repetitive current waveforms together forming a spatial current pattern for application to the array to generate voltage signals at the electrodes with respect to a common ground, for use in forming an electrical impedance image of at least part of a volume in the body;

control means for operating each of said voltage-to-current converters to apply the repetitive current waveforms to the current patterns in synchronism to said electrodes a multiplicity of times, said control means including said waveform means for generating, applying and removing a plurality of repetitive waveforms to and from all of said voltage-to-current converters simultaneously to power said plurality of electrodes simultaneously, said waveform means having a single master clock for use with all of said voltage-to-current converters and a common read-only memory with a digitally stored sinusoid for use in providing the repetitive waveforms;

separate voltmeter means connected to each electrode for measuring individual voltages at each electrode with respect to the common ground due to the multiplicity of concurrent patterns for use in imaging at least part of the volume of the body;

image means for receiving the voltages and forming an impedance image therefrom; and a calibration voltmeter, a current-to-voltage converter connected between said electrodes and the calibration voltmeter for converting current from each electrode into voltage to be measured by the calibration voltmeter, and switching mens connected to the current-to-voltage converter and the calibration voltmeter for calibrating each of said voltage-to-current converters separately.

14. An apparatus according to claim 13, wherein the switching means and calibration voltmeter are computer-controlled.

* * * * *